United States Patent [19]
Phan et al.

[11] Patent Number: 5,234,443
[45] Date of Patent: Aug. 10, 1993

[54] ENDOSCOPIC KNOT TYING APPARATUS AND METHODS

[75] Inventors: Cu N. Phan; Marshall L. Stoller, both of San Francisco, Calif.

[73] Assignee: The Regents of the University of California, Oakland, Calif.

[21] Appl. No.: 736,170

[22] Filed: Jul. 26, 1991

[51] Int. Cl.⁵ .............................................. A61B 17/00
[52] U.S. Cl. .................................... 606/148; 606/144; 606/205
[58] Field of Search ............... 606/144, 148, 228, 139, 606/140, 205-207; 128/898

[56] References Cited

U.S. PATENT DOCUMENTS

| | | |
|---|---|---|
| 3,871,379 | 3/1975 | Clarke . |
| 3,985,138 | 10/1976 | Jarvik ................................. 606/144 |
| 4,602,635 | 7/1986 | Mulhollan et al. . |
| 4,635,638 | 1/1987 | Weintraub et al. ................. 606/147 |
| 4,641,652 | 2/1987 | Hutterer et al. ...................... 289/17 |
| 4,760,848 | 8/1988 | Hasson . |
| 4,923,461 | 5/1990 | Caspari et al. ....................... 606/149 |
| 4,935,027 | 6/1990 | Yoon ................................... 606/148 |
| 5,037,433 | 8/1991 | Wilk et al. ............................ 606/222 |

Primary Examiner—Stephen C. Pellegrino
Assistant Examiner—Gary Jackson
Attorney, Agent, or Firm—Townsend and Townsend Khourie and Crew

[57] ABSTRACT

A suture applying and tying device comprises at least one grasping device for securing a length of suture, a second grasping device for forming a loop in a length of the suture, and a pushing rod for advancing the loop towards tissue.

9 Claims, 18 Drawing Sheets

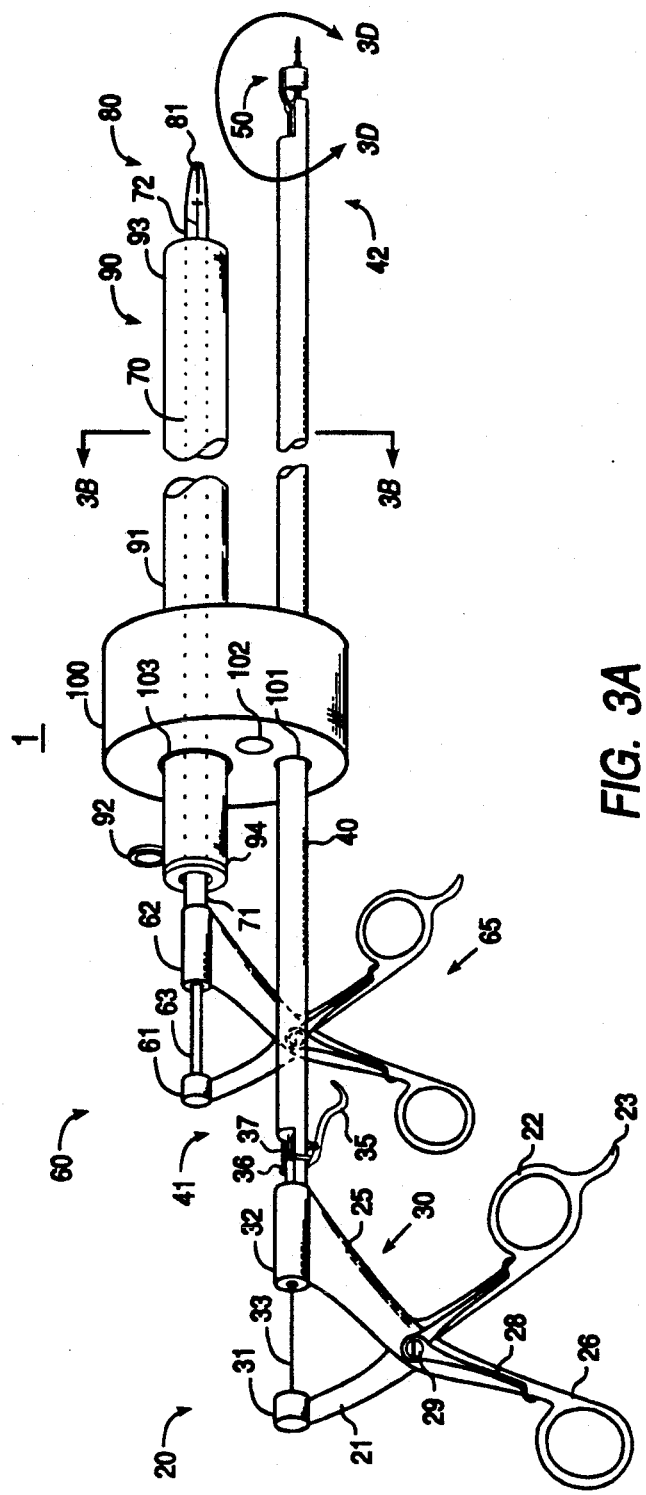
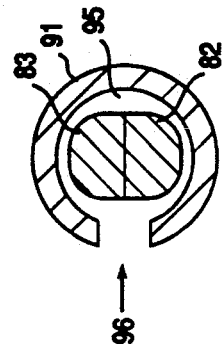
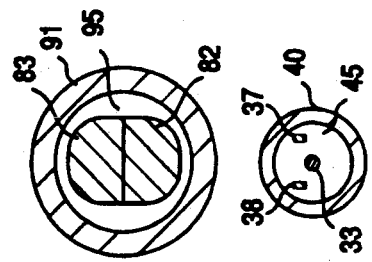
FIG. 3A
FIG. 3C
FIG. 3B

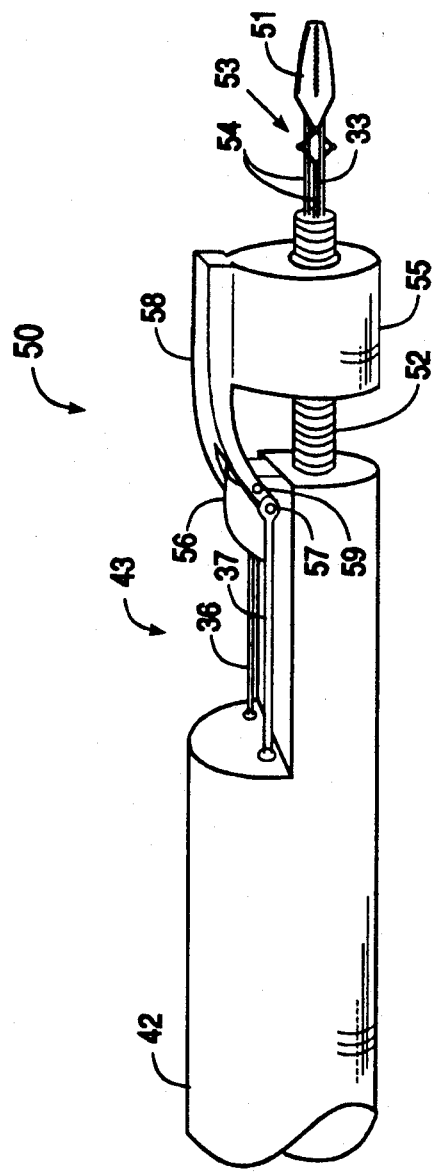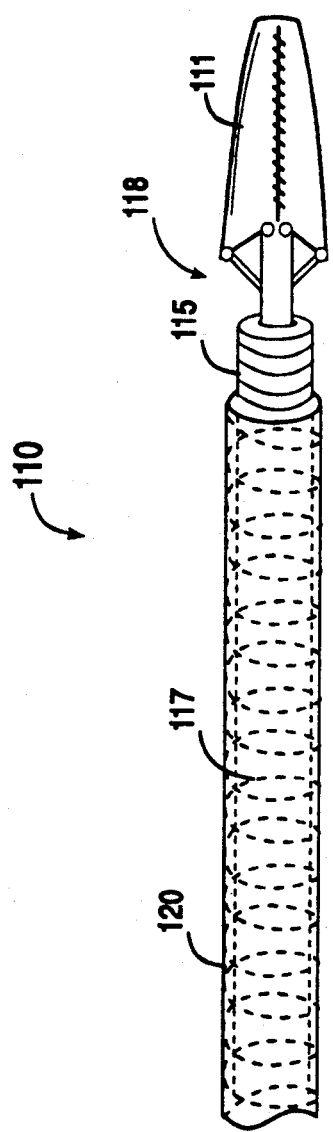
FIG. 3D
FIG. 3E

ENDOSCOPIC KNOT TYING APPARATUS AND METHODS

BACKGROUND OF THE INVENTION

1. Field of the Invention

The present invention relates generally to medical instruments and, more particularly, to apparatus and methods for applying and tying surgical thread within a limited workspace.

A variety of diseases, including many which previously would have required surgery, may be diagnosed and treated through medical scope-type instruments. Fiberoptic endoscopes are representative of these devices. Using an endoscope, a physician may confirm the presence of lesions found by other diagnostic methods as well as reveal some that would be missed. Endoscopes are typically introduced into a body orifice (e.g., the mouth or anus) and then advanced to the region of interest. Some scopes, such as laproscopes, are introduced through a small incision overlying the region of interest.

Since scoping instruments are introduced percutaneously or through a small puncture wound, they are less invasive than conventional surgery. In particular, a large incision for exposing a body region is not required. Thus, a patient is spared the morbidity and expense of major surgery. Furthermore, the instruments often cause minimal discomfort, and many procedures can be performed on an outpatient basis.

In addition to the diagnostic value from the direct visualization of an organ or body region, a variety of therapeutic procedures may be performed through an endoscope. Polypectomy and stricture dilation, for example, are routine endoscopic procedures. Other examples include laser ablation and electro-coagulation and cutting. Of particular interest to the present invention is endoscopic surgery, i.e., performing operative procedures through an endoscope.

Basic to any surgical technique, including endoscopic surgery, is the ability to coapt or "close" tissue. Tissue is usually coapted or approximated with surgical thread or suture by sewing together opposing edges. The suture is secured by tying knots at selected locations.

Without special instruments, knot tying is at best a bimanual task. Usually a knot is tied by holding one end of the thread while the other hand passes the opposite end of the tread under (or over) the first end. Alternatively, a loop may be formed on one end and slipped over the other end; this "slip knot" may then be advanced towards the tissue. A grasping instrument (e.g., a needle holder or a hemostat) may be used to facilitate the handling of thread, particularly fine or delicate thread, but two hands are still required. Single-handed techniques (e.g., staples, clips, tapes, and the like) are known for approximating tissue; nonetheless, two-handed sewing or "suturing" remains the most popular technique for closing surgical wounds.

Suturing techniques have not been well adapted to endoscopic surgery however. In contrast to an open surgical field in which a surgeon typically operates, the workspace available to an endoscopist (e.g., the lumen of a viscus) is typically located at a remote site within the body, often with very little room within which to work. Furthermore, operative techniques, including tissue coaptation, must be accomplished through one or more endoscopic ports or cannulas, which afford very little room for maneuvering. Thus, many procedures, including those which require bimanual dexterity such as knot tying, are not readily performed through an endoscope.

Therefore, it is desirable to provide improved apparatus and methods for applying and securing surgical thread within a remote and/or confined workspace. The apparatus should be able to reach these target locations while requiring minimal workspace. Furthermore, the techniques employed by the apparatus in securing suture should not be cumbersome to perform and should rely on dexterity skills which a surgeon already possesses. The present invention fulfills this and other needs.

2. Description of the Background Art

U.S. Pat. No. 4,641,652 describes an applicator for tying sewing threads, typically through an endoscope. The applicator, which comprises a coil at the end of a shaft, requires that the suture (thread and needle) be placed into the applicator prior to insertion through the endoscope. In operation, the needle must be pulled through the coil of the applicator, making the entire technique fairly cumbersome to perform.

Similar apparatus are known. U.S. Pat. No. 4,760,848 describes a knot-tying instrument having a pair of jaws at a distal end of a tube. The jaws may be used for carrying a surgical needle which is attached to a length of suture. The suture may include a performed loop with a slip knot that allows the suture to be tied by passing the needle back through the loop.

U.S. Pat. No. 4,602,635 describes a surgical knot-tying device comprising a cylindrical rod having an angularly cut end which is used in combination with a cannula; a knot is tied externally and advanced forward to the tissue being approximated.

U.S. Pat. No. 4,923,641 describes a suturing instrument for use in arthroscopic surgery. The instrument, which resembles a conventional grasper and forceps-type microsurgical instrument, includes a hollow tip for engaging tissue to be sutured and a recess for securing a hollow tubular needle. Like the device of U.S. Pat. No. 4,602,635, this device requires a knot to be tied externally and advanced forward to the tissue being sutured.

U.S. Pat. No. 3,871,379 describes a laproscopic needle and forceps for use in combination with two trocars; as with the two foregoing patents, a knot is secured outside of the body and then advanced to a desired location.

The disclosures of each of the foregoing references are hereby incorporated by reference.

SUMMARY OF THE INVENTION

The present invention comprises apparatus and methods for applying and tying surgical thread within a limited workspace. The device of the present invention includes one or more grasping devices for manipulating surgical thread, with one of the grasping devices including an outer "pushing shaft".

The graspers may have a variety of configurations but should be sufficiently small to allow passage through a small port, such as an endoscopic port. In an exemplary embodiment, a grasper of the present invention includes a main shaft having proximal and distal ends. Pivotable jaws are disposed at the distal end, with a handle secured at the proximal end. Under control of hand movements at the proximal end, the jaws may grasp objects such as suture and needle. The handle includes a moveable hand member pivotally mounted to a stationary hand member and includes means for actuating the jaws. Finger rings and the like may be provided for facilitating movement of the hand members.

The pushing shaft comprises an elongate tubular body having proximal and distal ends with a central lumen extending therethrough. While the shaft may have a variety of cross-sectional configurations, in a preferred embodiment the shaft defines a generally cylindrical tube with a longitudinal cutout. The lumen of the shaft should be sufficiently large to accommodate one grasper therethrough. However, it should not be so large as to prevent its passage through a small port.

The device of the present invention may include one or more adapters for securing the components to a scoping instrument. The adapter includes a generally cylindrical housing having one or more ports for the insertion of components, instruments, and the like.

In a method of the present invention, a needle-bearing suture is passed through a tissue and then secured to the tissue by forming slip knots. Each slip knot is formed as follows. The needle-bearing end of the suture is secured with one of the graspers. A second grasper, which has a flexing distal end, forms a loop by twirling a segment of the suture. After formation of the loop, the second grasper (still within the loop) grabs the free end of the suture and pulls it through the loop. The pushing shaft may then be advanced for securing a slip knot at the tissue surface.

In an alternative method, two loops are formed along the shaft of a cylindrical trough while a corresponding end is held by a first grasper. The first loop is snagged and pulled through the second loop by a hook-bearing grasper. The pushing shaft may then be advanced for securing a slip knot at the tissue surface.

BRIEF DESCRIPTION OF THE DRAWINGS

FIG. 3A is a lateral view of a suture applying and knot tying device of the present invention.

FIG. 3B is a cross-sectional view of the device of FIG. 3A, taken along line 3B—3B.

FIG. 3C is a cross-sectional view showing an alternate construction of a pusher shaft of FIG. 3B.

FIG. 3D is a detailed lateral section showing a grasping member, taken along line 3D—3D of FIG. 3A.

FIG. 3E is a detailed lateral section showing an alternative construction for the grasping member of FIG. 3D.

DETAILED DESCRIPTION OF THE SPECIFIC EMBODIMENTS

Introduction

Referring now to FIGS. 1A-J, basic techniques for coaptating tissue using surgical thread or suture are illustrated. In general, tissue is coapted by sewing together tissue edges. A surgical thread, typically bearing a needle at one end, is passed through the tissue. The thread is secured by placing knots at selected locations.

Figure 1A:
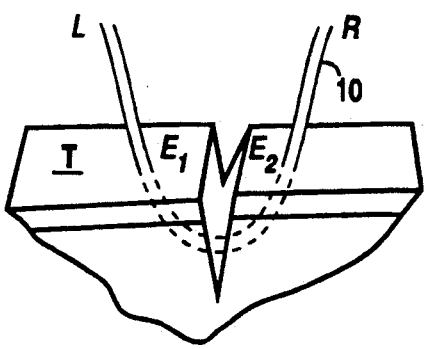
FIGS. 1A-J illustrate the initial step of forming a knot to coapt tissue, the tying of a half hitch.
Figure 1B:
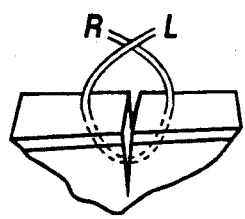
Figure 1C:
Figure 1F:
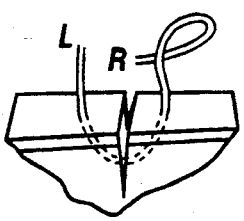
Figure 1G:
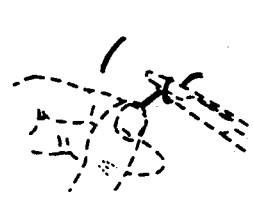
Figure 1D:
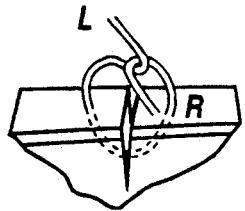
Figure 1E:
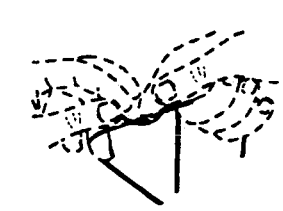
Figure 1H:
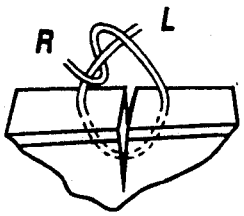
Figure 1I:
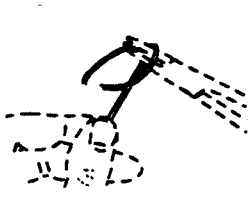
Figure 1J:
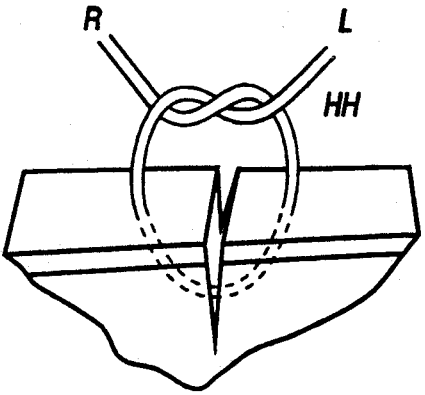

The simplest of all surgical knots is the "half hitch" (shown as HH in FIG. 1J). It (and its variant, the surgeon's knot) forms the basis for most surgical knots. In fact, the majority of surgical knot tying is the process of creating successive half hitches.

As shown in FIG. 1A, the first step of coaptating tissue T is passing a suture 10 (shown with its needle detached) through two free edges $E_1$, $E_2$ of the tissue. The edges are then approximated by forming a half hitch HH in the suture. Different techniques exist for performing this step.

In one technique, popular for hand (noninstrument) tying, a half hitch is formed by crossing one end of the thread over or under the other. Illustrated by FIGS. 1B-E, the two ends R, L of the suture 10 are crossed to form a closed loop, with one end or the other passing through the loop.

In another technique, popular for instrument-assisted tying, a half hitch is formed by slipping a loop formed at one end of the thread over the other end. Illustrated by FIGS. 1F-I, the right end R is twisted to form a loop; this is then slipped over the free end of the left end L. At the completion of either technique, a half hitch HH is formed and advanced towards the tissue T, as shown in FIG. 1J.

Figure 2A:
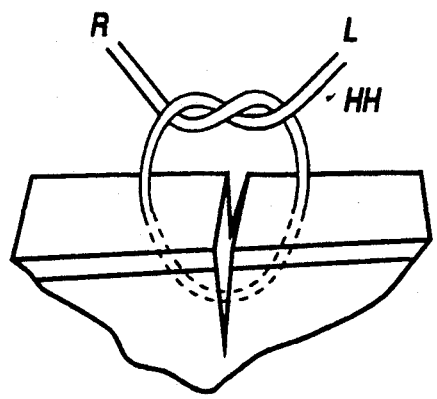
FIGS. 2A-C illustrate completion of square and surgical knots.
Figure 2B:
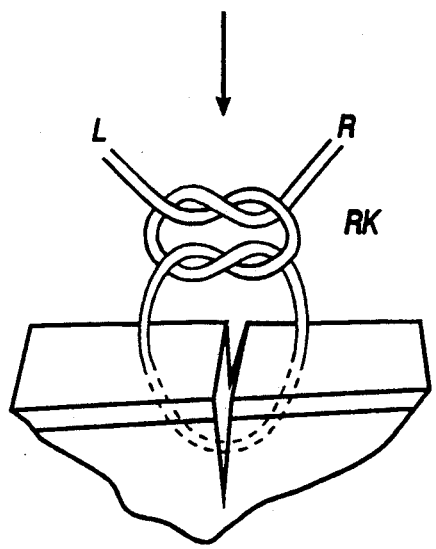
Figure 2C:
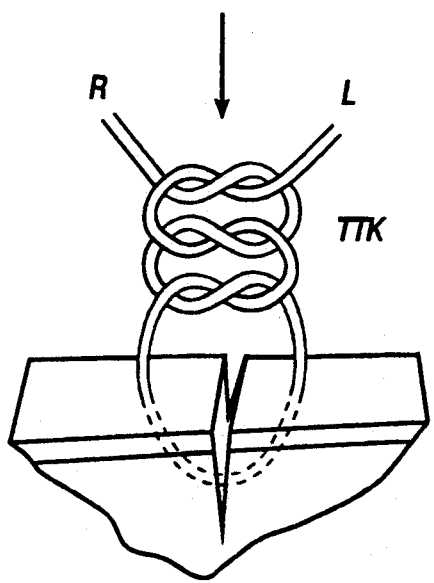

Shown in FIGS. 2A-C, common surgical knots may be created by tying additional half hitches. If a second half hitch of a different type than the first half hitch (e.g., "over" instead of "under" crossing) is placed, a square or reef knot RK is created, as shown in FIG. 2B. The reef knot is preferred over a granny knot, which is a weaker knot formed when the second half hitch is the same type as the first. In surgery, the knots most often employed include several reversing half-hitches or throws which form a series of reef knots, such as the surgical or triple throw knot TTK shown in FIG. 2C.

A particular problem of tying surgical knots within a limited workspace, such as an endoscopic workspace, is the space required for making initial and/or subsequent loops. One approach is to form the loops external to the workspace. This approach, employed by several of the prior art knot tying devices, is cumbersome to perform, requiring awkward steps such as pulling a needle through one or more coils.

Preferred Embodiments

The following discussion will focus on the coaptation of tissue during endoscopy. The present invention, however, is not limited to one particular application or environment. Instead, the present invention may be advantageously employed for applying and tying thread, including suture materials, at a variety of locations which are remote and/or have limited working space. Those skilled in the art will appreciate techniques other than tissue coaptation, e.g., ligating vessels, placing retention sutures, and the like, which may be practiced with the present invention. Furthermore, the apparatus of the present invention may be adapted for use with a variety of other scoping instruments.

The device of the present invention is suitable for use with substantially all suture materials, particularly those which have a surgical needle attached at one end. The length of suture employed is not critical and may vary widely depending on the intended application. Typical sutures have a length ranging from about 10 to 40 cm or more. The suture may be formed from any conventional suture material, including silk, cotton, nylon, gut, chromic gut, wire, Prolene, and the like. The needle employed may be a conventional surgical needle, including both straight and curved types. While not required by the present invention, a curved needle is generally easier to manipulate when tying with instruments.

The knot formed with the device of the present invention will be a half hitch, created initially as a slip knot. The knot allows a free loop to be formed which may then be cinched tight against the free end of the suture, thus forming a particularly stable knot for approximating tissue. Additional half hitches or slip knots may be tied and advanced for creating reef and surgical knots.

The device of the present invention includes one or more grasping instruments, at least one of which may include an outer "pushing" shaft. The graspers may have a variety of configurations, but should be sufficiently small to allow passage through an endoscopic port or cannula. In an exemplary embodiment, a grasper of the present invention includes a main body or shaft having jaws at a distal end, with a handle secured to a proximal end. The jaws will be able to firmly grasp objects, such as suture and needle, under control of hand movements at the proximal end. The handle will typically have a movable hand member pivotally mounted to a stationary hand member, and will include means for actuating the jaws. The hand members may include finger rings for facilitating movement of the grasper and the jaws. In addition, the handle will typically include a spring or clamp for closing (or opening) the stationary and moveable handle members, thereby closing the jaws when the instrument is at rest.

The pushing shaft or tube comprises an elongate tubular body having proximal and distal ends, with a central lumen extending therethrough. The shaft may have any crosssectional configuration, but typically will be round in shape. The diameter of this shaft is not critical, but will usually be sufficiently large to accommodate one grasper within its central lumen, yet sufficiently small to allow its passage through a small port or cannula. The shaft will have a length sufficient to extend from an operator's hand to a body region of interest, and will typically be from about 15 to 75 cm. Additionally, the shaft will include a handle or the like at its proximal end for advancing and retracting the shaft. The tubular body of the shaft may include a cutout along one side for facilitating tissue exposure, maneuvering of instruments, and preventing accumulation of fluids.

The device of the present invention may also include one or more adapters for fitting the grasper(s) and/or the pushing shaft to a scoping device, such as an endoscope. The adapter will include a housing suitable for attachment to a scope instrument and having one or more ports. The ports will accommodate the pushing shaft and grasper(s), with the grasper port typically having a smaller diameter. Additional ports may be provided, for example, to accommodate additional instruments, lights, air hoses, water hoses, and the like.

All components of the apparatus of the present invention may be constructed of metal, preferably stainless steel. The entire device of the present invention is autoclavable. Alternatively, some or all components of the apparatus of the present invention may be constructed of plastics, resins, organic polymers, and the like; when so constructed, the device of the present invention may be economically disposed, hence eliminating the risk of spreading contagious diseases through contaminated instruments.

Referring now to FIGS. 3A–E, a suture applying and knot tying device 1 constructed in accordance with the principles of the present invention will be described. Device 1 includes a first grasper 20, a second grasper 60, and a pushing shaft 90. Device 1 may also include an adapter 100 for stabilizing the pushing shaft 90 and the graspers 20, 60 at one end of an endoscope.

First grasper 20 includes an elongate tube or barrel 40 having a proximal end 41 and a distal end 42. Tube 40 includes a central lumen 41 extending from the proximal end 41 to the distal end 42. Tube 40 includes a grasping member 50 at its distal end and a handle 30 at its proximal end.

Shown particularly in FIG. 3D, grasping member 50 comprises a distal housing 55 having jaws 51 secured distally. In particular, a flexible coil 52, attaches the housing 55 to the distal end 42. The coil 52, which passes through the housing 55, connects with the jaws 51 through a pair of rods 54. Jaws 51 include a pivot assembly 53 which opens and closes the jaws in response to movement of a grasping cable 33, which extends proximally to attach to the handle 30.

To flex the jaws 51, distal housing 55 is also connected to the distal end 42 through a flange 58. Flange 58 is pivotally attached to a connector hub 56 which is disposed within a semicircular cutout 43 of the distal end 42, the flange 58 being attached by connector pins 59 which pass through hub 56. Flexing motion of the grasping member 50 is provided by rods or cables 36, 37 which push the flange 58 causing member 50 to pivot about the pins 59 when the rods or cables are advanced. The cables 36, 37 are pivotably attached to the flange 58 by connectors 57. The cables extend proximally and attach to a finger trigger 35 by connector pins. When the cables 36, 37 are advanced (by activating trigger 35), the flange 58 is drawn upward and rearward, thus bending the grasping member 50 at the coil 52.

With particular reference to FIG. 3E, an alternative to the grasping member 50 is shown. Grasping member 110 comprises grasping jaws 111 disposed at the end of a flexible coil 115. Jaws 111 include a pivot assembly 118 for receiving an advancing means (e.g., cable 33). In this embodiment, the shaft 40 is replaced with a flexible outer sheath 120, which may be formed from plastics, resins, or organic polymers. Sheath 120 includes proximal and distal ends, its proximal end attaching to the handle 30. From its distal end, the helical coil 115 extends outward. Grasping member 110 may also include a second coil 117 disposed within a lumen of the sheath 120, the second coil serving to transmit axial and torsional forces from the handle 30. When the trigger 35 is activated, the grasping member 110 will bend. The mechanism of bending is similar to that of a flexible endoscope, which is known in the art.

Grasper 20 includes a handle 30 secured to the proximal end 41 of tube 40. Handle 30 comprises a stationary handle member 25 having a movable handle member 21 pivotally mounted by a pivot pin or screw 29. The stationary handle member 25 includes a thumb ring 26 at one end and a receiving barrel 32 at its other end. Handle member 21 includes a finger ring 22 which may include a finger flaring 23. Handle member 21 includes a base 31 for receiving the cable 33. Cable 33 is secured to the base 31 and then passes through the barrel 32, through the lumen 45, through the coil 52, for attachment to the pivotable member 53 of jaws 51. The handle members 21, 25 are maintained in an closed or retracted position by spring or clamp 28 which forces the thumb ring 26 and finger ring 22 together, thus closing the jaws when the instrument is at rest. When intended for certain applications (e.g., neurological surgery), however, it may be desirable to maintain the handle members 21, 25 in an open or distracted position; however, the jaws will still typically be closed when the instrument is at rest. The spring may be secured to the members by the screw 29.

The second grasper 60 includes an elongate shaft 70 (shown in broken line) having a proximal end 71 and a distal end 72. At the distal end 12 the shaft 70 includes a grasping member 80 having a pair of pivotable jaws 81. The jaws 81 may be of a conventional design and may include teeth, serrations, and the like, or may be flat. The shaft 70 may include upper 83 and lower 82 halves for controlling the jaws 81. Grasper 60 includes a handle 65 secured to the proximal end 71 of tube 70. Handle 65 may be of the same or of similar construction as the handle 30 except that its base 61 receives a rod 63 which then passes through a barrel 62 for actuating the grasper 80 (e.g., by shifting the upper half 83 relative to the lower half 82).

Pushing shaft 90 comprises an elongate tubular body 91 having a proximal end 94 and a distal end 93. A central lumen 95 extends from the proximal end 94 to the distal end 93, and has a diameter sufficient to accommodate the tubular shaft 70 of grasper 60. The proximal end 94 of pusher 90 includes a slider handle or grip 92 which may be in the form of a ring or other structure which is easy to grasp. While the tubular body 91 generally defines a rod, it exact configuration is not critical. A cutout or slot 96 may be provided along one side of the tube 91 for facilitating tissue exposure, maneuvering of instruments, preventing accumulation of fluids, and the like.

The adapter 100 includes a generally cylindrical housing having a port 101 for the grasper 20 and a port 103 for the pushing shaft 90. In an exemplary configuration, shaft 70 of grasper 60 will pass through the lumen 95 of pusher 90, and hence will also pass through the port 103. Additional ports or openings may be provided, such as port 102, for accommodating additional instruments and the like.

Figure 4A:
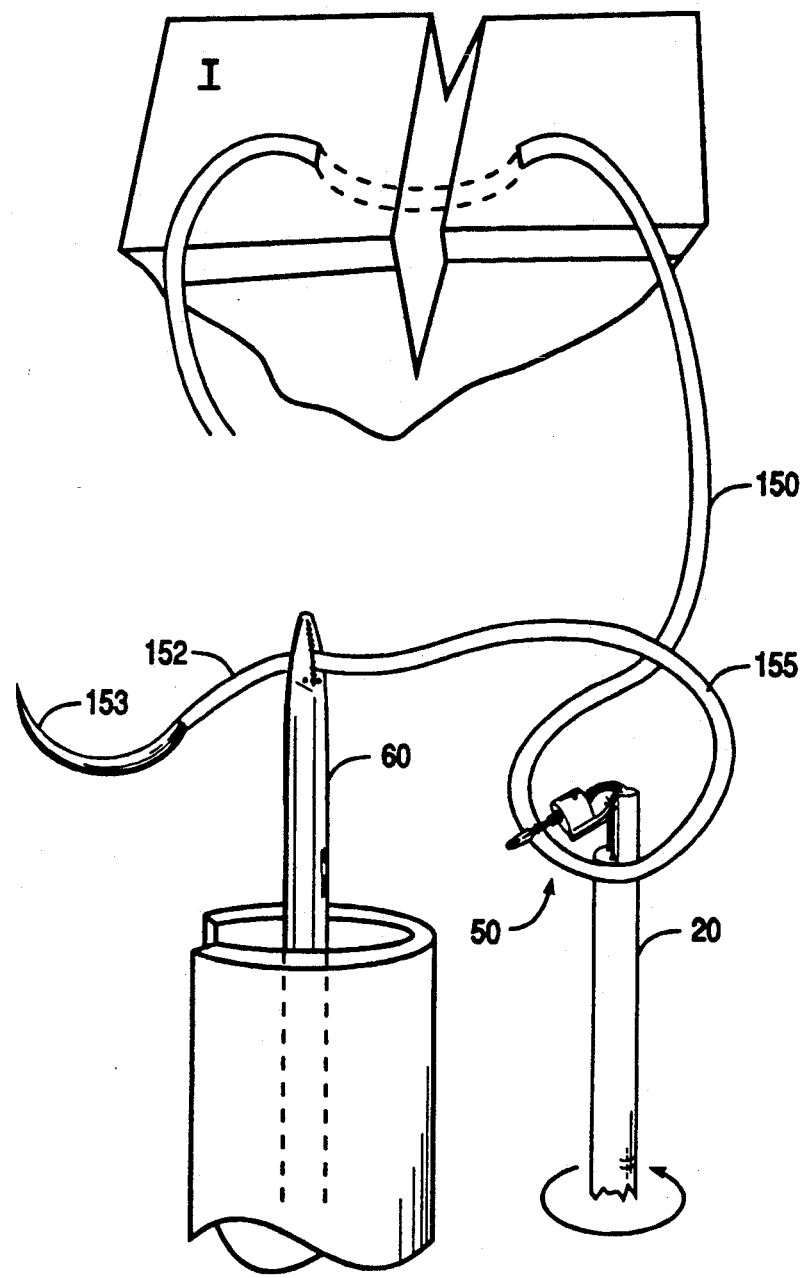
FIGS. 4A-B are lateral sections illustrating the formation of a knot with the embodiment of FIG. 3A.
Figure 4B:
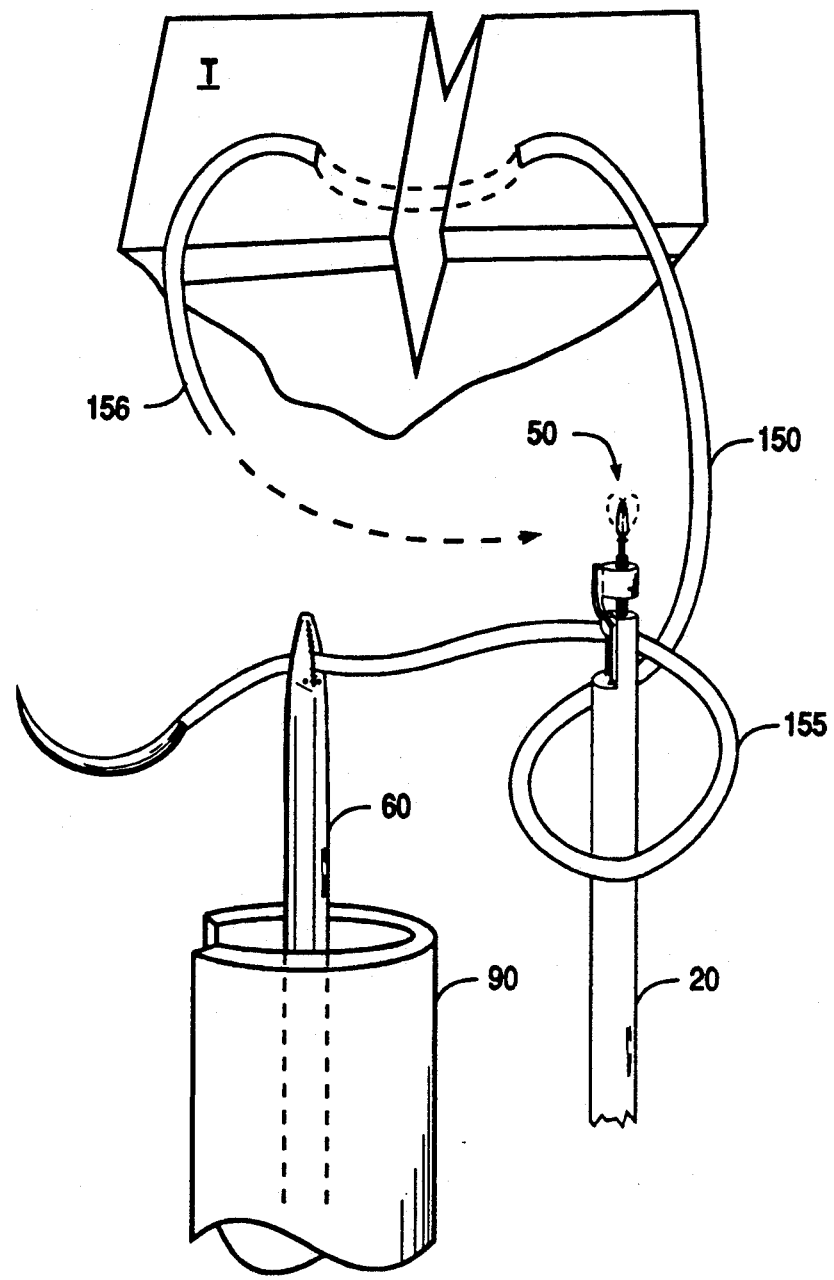

Referring now to FIGS. 4A-B, the operation of device 1 will now be described. As shown in FIG. 4A, a suture 150 has been passed through opposing edges of tissue T. In particular, suture 150 includes a needle 153 which has been driven through the tissue T by either grasper 60 or grasper 20. Next, the grasper 20 is maneuvered to create a loop 155. In particular, the grasping member 50 is flexed so that it entraps at least a portion of suture 150. At the same time, the needle 153 or the needle end 152 of the suture is secured With the grasper 60. The grasper 20 is then rotated around its longitudinal axis to create the loop 155.

As shown in FIG. 4B, the grasping member 50 is then straightened and advanced towards a free end 156 of the suture 150. Once positioned, the grasping means 50 may then grab the free end 156 and pulls it through the loop 155. Finally, the knot is secured and advanced towards the tissue by pusher 90 by thrusting the ring 92 forward.

Figure 5:
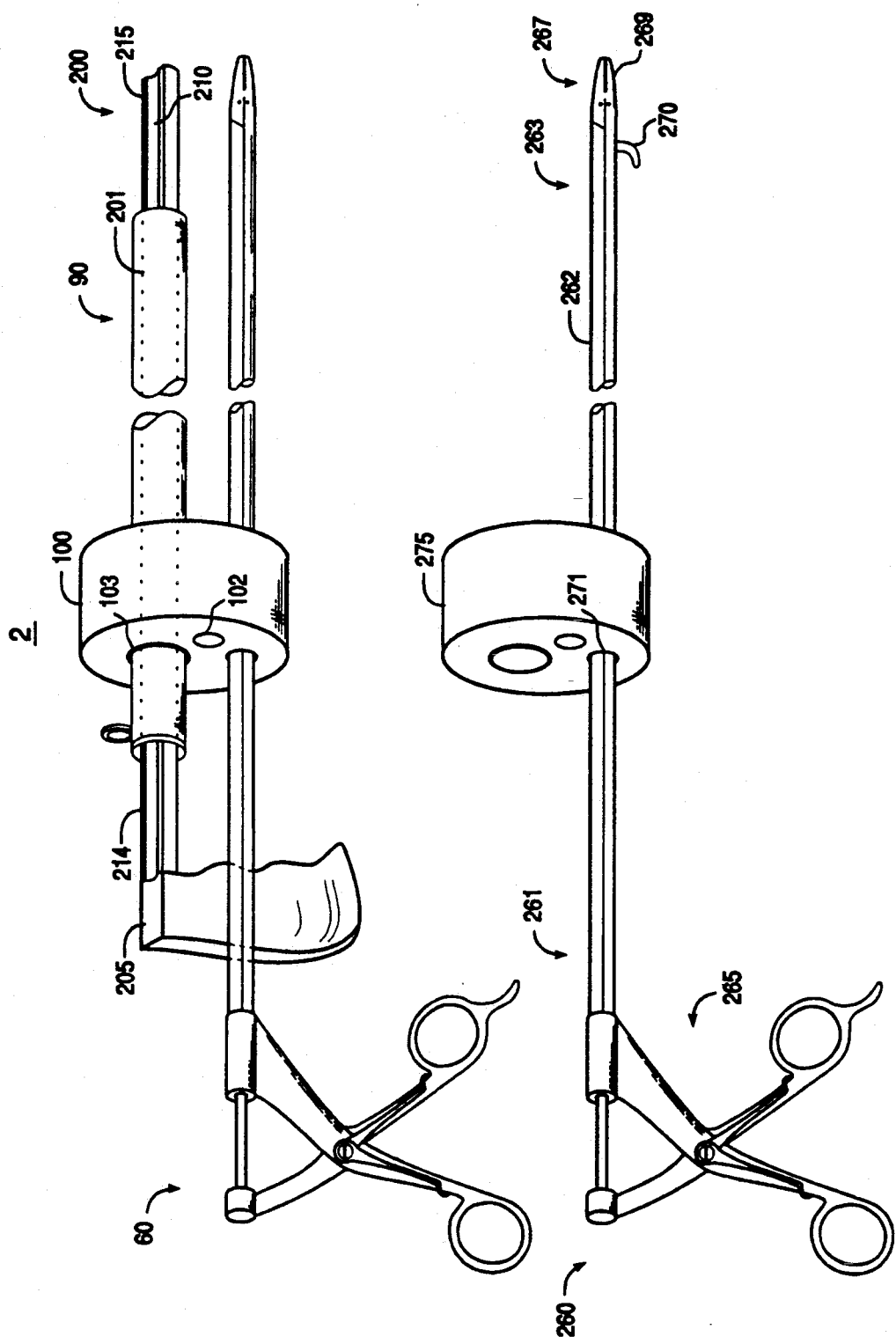
FIG. 5 is a lateral view of a second embodiment of the present invention.

Referring now to FIG. 5, a second embodiment of the present invention will be described. A suture applying and knot tying device 2 includes two graspers, a pushing shaft, and a semicircular or semicylindrical trough. Device 2 may also include one or more adapters for stabilizing the components.

The device 2 shares the following components of device 1: grasper 60, pushing shaft 90, and adapter 100. In addition, device 2 includes a semicylindrical trough 200 and a grasper 260 having a hook 270.

Grasper 260 includes an elongate shaft 262 having a proximal end 261 and a distal end 263. At the distal end 263 the shaft 262 includes a grasping member 267 having a pair of pivotable jaws 269, which may be of a conventional design. The grasper 260 includes a handle 265 secured to the proximal end 261 of the shaft 262. As described thus far, the grasper 260 may have the same or a similar design as the grasper 60.

Grasper 260 is provided with an additional component however. Disposed along the distal end 263, grasper 260 includes a hook 270. While the exact placement of hook 270 is not critical, the hook 270 should be positioned proximate the grasping member 267. Hook 270 may be located along any side of the shaft 262. In an exemplary embodiment, the hook 270 is secured to a ventral surface the shaft 262.

The semicylindrical trough 200 of the device 2 includes an elongate, semicylindrical shaft 201 having a proximal end 214 and a distal end 215. Extending from the proximal end 214 to the distal end 215, shaft 201 includes a trough 210 disposed substantially along a single side of the shaft 201. At the proximal end 214, the semicylindrical trough 200 includes a handle 205 in the form of a grip. The shaft length should be sufficient to extend from an operator's hand to a body region of interest and will typically be from about 15 to 75 cm. As with the pushing shaft 90, the diameter of the shaft 201 is not critical but should be sufficiently large to allow suture to be looped around its distal end 215; it should be sufficiently small, however, to allow its passage through the lumen of the pushing shaft 90.

As shown in FIG. 5, an exemplary configuration of the device 2 includes the pusher 90 and the grasper 60 disposed within the port 103 of the adapter 100, with the trough 200 passing through the lumen of the pusher 90. Grasper 60 may also be slidably secured to a length of pusher 90. Grasper 260 may be inserted through the port 102 of adapter 100. Alternatively, a second adapter 275 may be employed, with grasper 260 passing through a port 271 of the adapter.

Figure 6A:
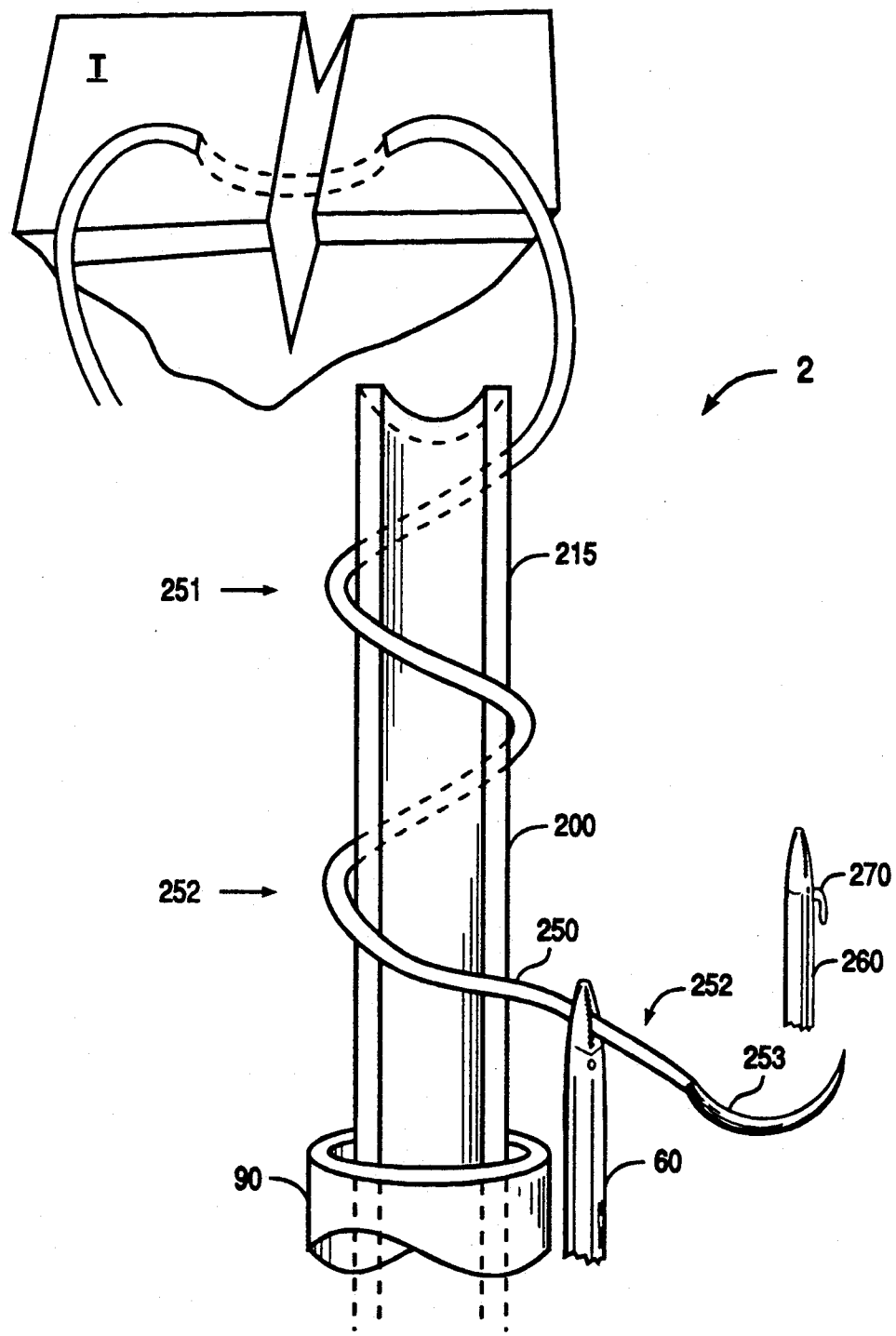
FIGS. 6A-B are lateral sections illustrating the formation of a knot with the embodiment of FIG. 5.
Figure 6B:
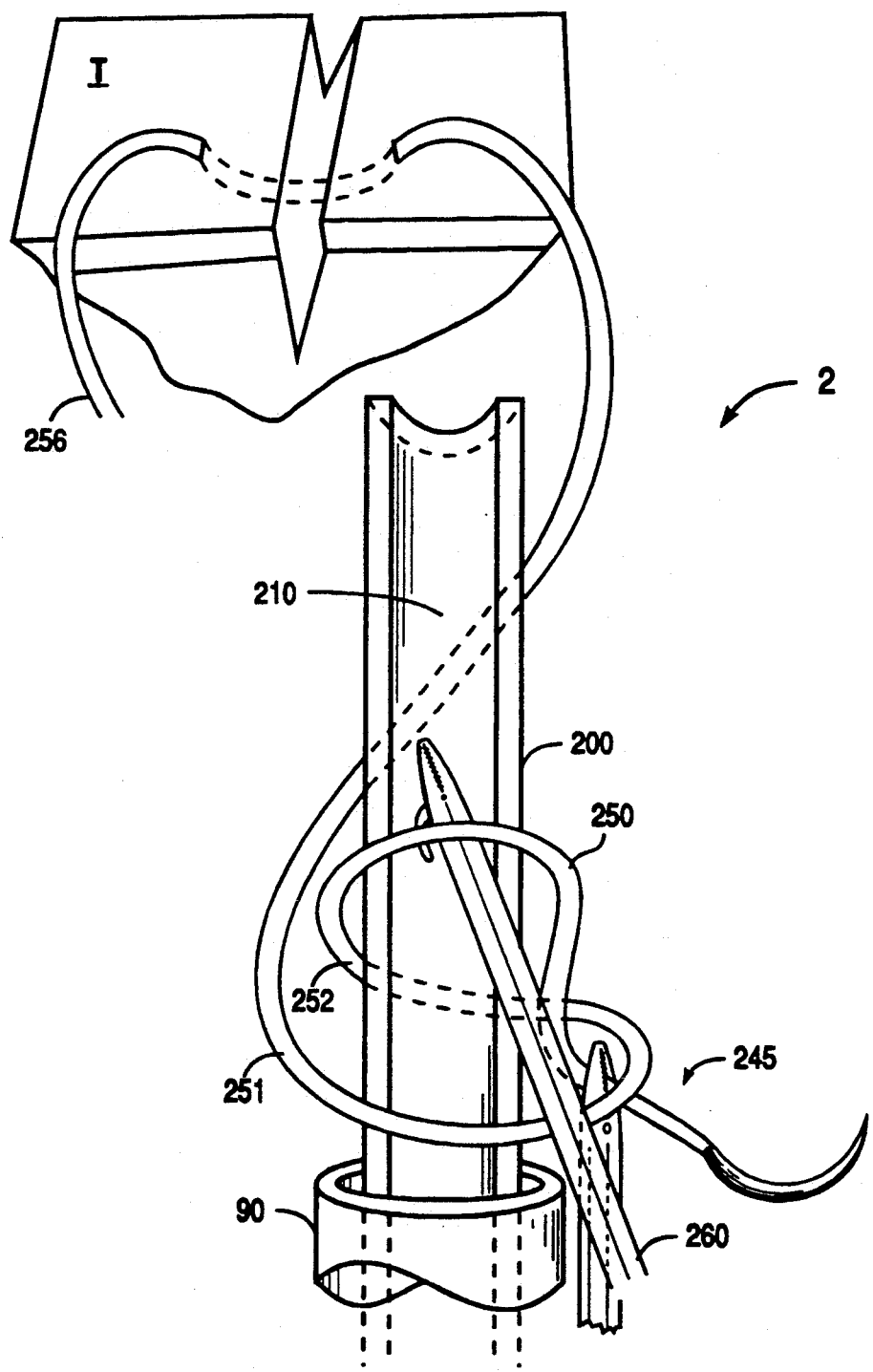
Figure 6C:
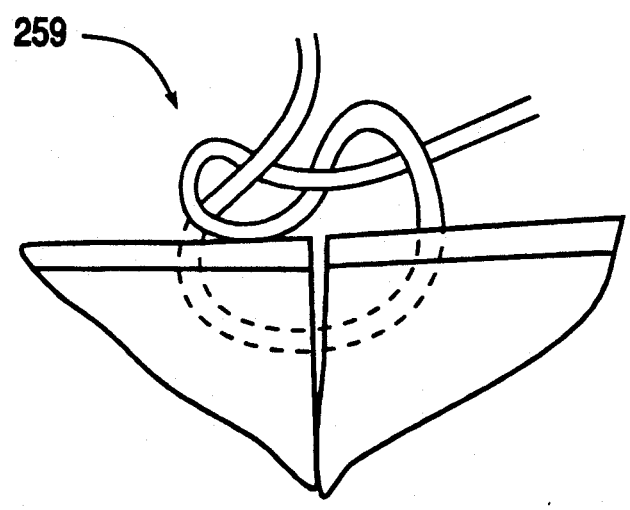
FIG. 6C is a diagrammatic view of tissue having the slip knot of FIGS. 6A-B.

Referring now to FIGS. 6A-B, the operation of device 2 will now be described. As shown in FIG. 6A, a suture 250 having a needle 253 has been driven through the tissue T. Next, the needle-bearing segment 252 of the suture 250 is secured with the grasper 60, which may be slidably attached to the semicylindrical trough 200. The trough 200 is then rotated or twirled (e.g., by twisting the handle 205) so that two loops 251, 252 are created around its distal end 215. As shown in FIG. 6B, the hook-bearing grasper 260 pulls the loop 251 over loop 252; the grasper 260 is then advanced into the trough 210 and then retracted under loop 252. Grasper 260 is then advanced forward to grasp a free end 256 of the suture 250. Finally, the pusher 90 is advanced forward to create the slip knot 259, as shown in FIG. 6C.

Figure 7A:
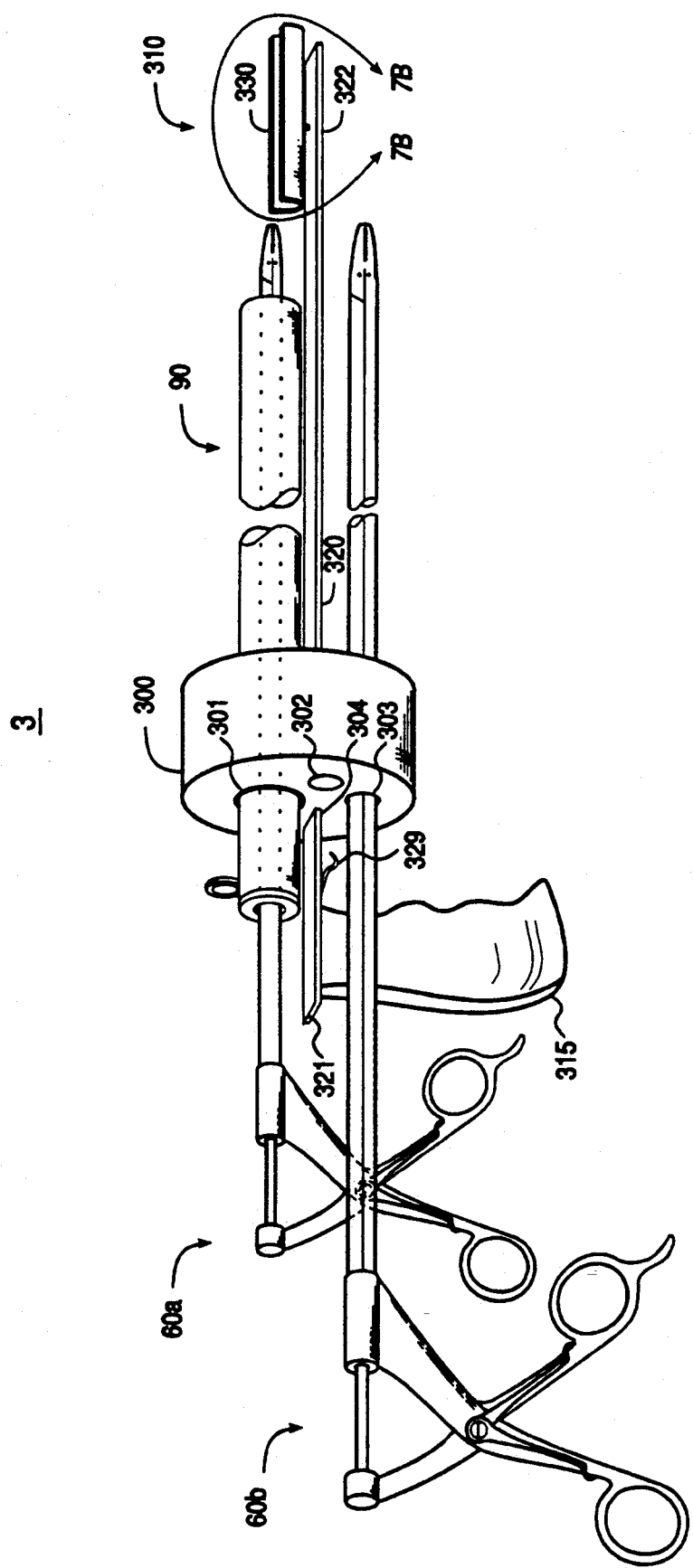
FIG. 7A is a lateral view of a third embodiment of the present invention.
Figure 7B:
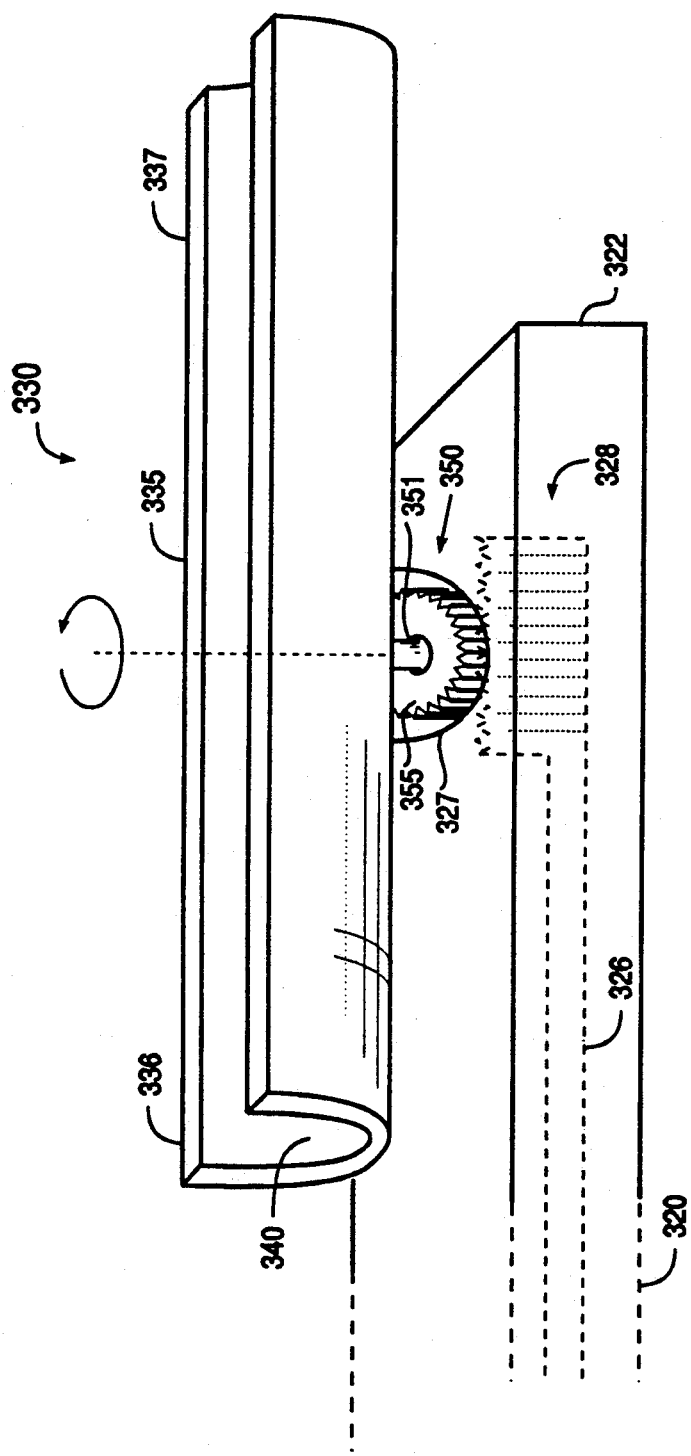
FIG. 7B is a detailed lateral section of a semicircular trough of FIG. 7A, taken along line 7B—7B.

Referring now to FIGS. 7A-B, a third embodiment of the present invention will be described. A suture applying and knot tying device 3 includes two graspers, a pushing shaft, and a rotating semicylindrical trough. Device 3 may also include one or more adapters for stabilizing the components.

The device 3 includes the following previously described components: two graspers 60 (60a and 60b) and pushing shaft 90. In addition, device 3 includes a rotating semicylindrical trough device 310 and an adapter 300 suitable for stabilizing the trough 310 as well as the other components.

The semicylindrical rotating trough device 310 of the device 3 includes an elongate platform or support 320 having a proximal end 321 and a distal end 322. At the distal end 322, support 320 includes a rotating trough 330 (described in further detail hereinbelow). At the proximal end 321, the rotating trough device 310 includes a handle 315, which may be in the form of a grip.

The length and configuration of the support 320 are not critical. While shown as a substantially planar structure, the support 320 may have a variety of configurations, including an elongate tube or shaft or the like. Support 320, which is disposed beneath the grasper 60a and the pusher 90 when inserted into the adapter 300, should be of sufficiently narrow construction as not to interfere with the operation of the other components. The length of the support should be sufficient to extend from an operator's hand to a body region of interest and will typically range from about 15 to 75 cm. Its width should be sufficiently small to allow its insertion into a port, such as a port 304 of the adapter 300.

As shown in FIG. 7A, an exemplary configuration of the device 3 includes the pusher 90 and the grasper 60a disposed within a port 301 of the adapter 300, with the body of the grasper 60a disposed within the lumen of the pusher 90; the grasper 60b, which is of the same construction as grasper 60a, may be inserted through the port 303 of the adapter 300. Rotating trough member 310 is inserted in the port 304 of the adapter 300, thus positioning it beneath the pusher 90 and the grasper 60. Those skilled in the art will appreciate adapter configurations other than that shown in FIG. 7A which will accomplish the same or similar functionality of the device 3.

With particular reference to FIG. 7B, the construction of the rotating trough 330 will b described. Rotating trough 330 includes a semicylindrical body 335 having a proximal end 336 and a distal end 337, with a trough 340 disposed substantially along an upper or superior surface of body 335 and extending from the proximal end 336 to the distal end 337. Rotating trough 330 is attached to the distal end 322 of the support 320 through a gear assembly 350.

Gear assembly 350 includes a shaft 351 and a gear 355. Shaft 351 is rotatably mounted to the distal end 322 and passes through an opening 327 thereat. At an opposite end of the shaft 351, the trough body 335 is attached. Shaft 351 includes the gear 355 which mates with a sliding bar 326. Sliding bar 326 is disposed within the support 320 and includes serrations or gear teeth 328 distally for engaging the gear 355. At the proximal end 321 of the platform 320 (just distal to handle 315), sliding bar 326 attaches to a finger trigger 329. In operation, the rotating trough 330 is rotated by retracting the trigger 329. In particular, retraction of the trigger 329 moves the slidable bar 326 which then rotates the shaft 351 (through gears 328 and 355). In a preferred embodiment, slidable bar 326 moves a linear distance sufficient to rotate the trough member 335 substantially 180 degrees. The trigger 329 and/or the bar 326 may include clamps, springs, or the like for maintaining the trigger in an open or non-retracted position when the instrument is at rest, thereby maintaining the trough 335 in axial alignment with support 320.

Figure 8A:
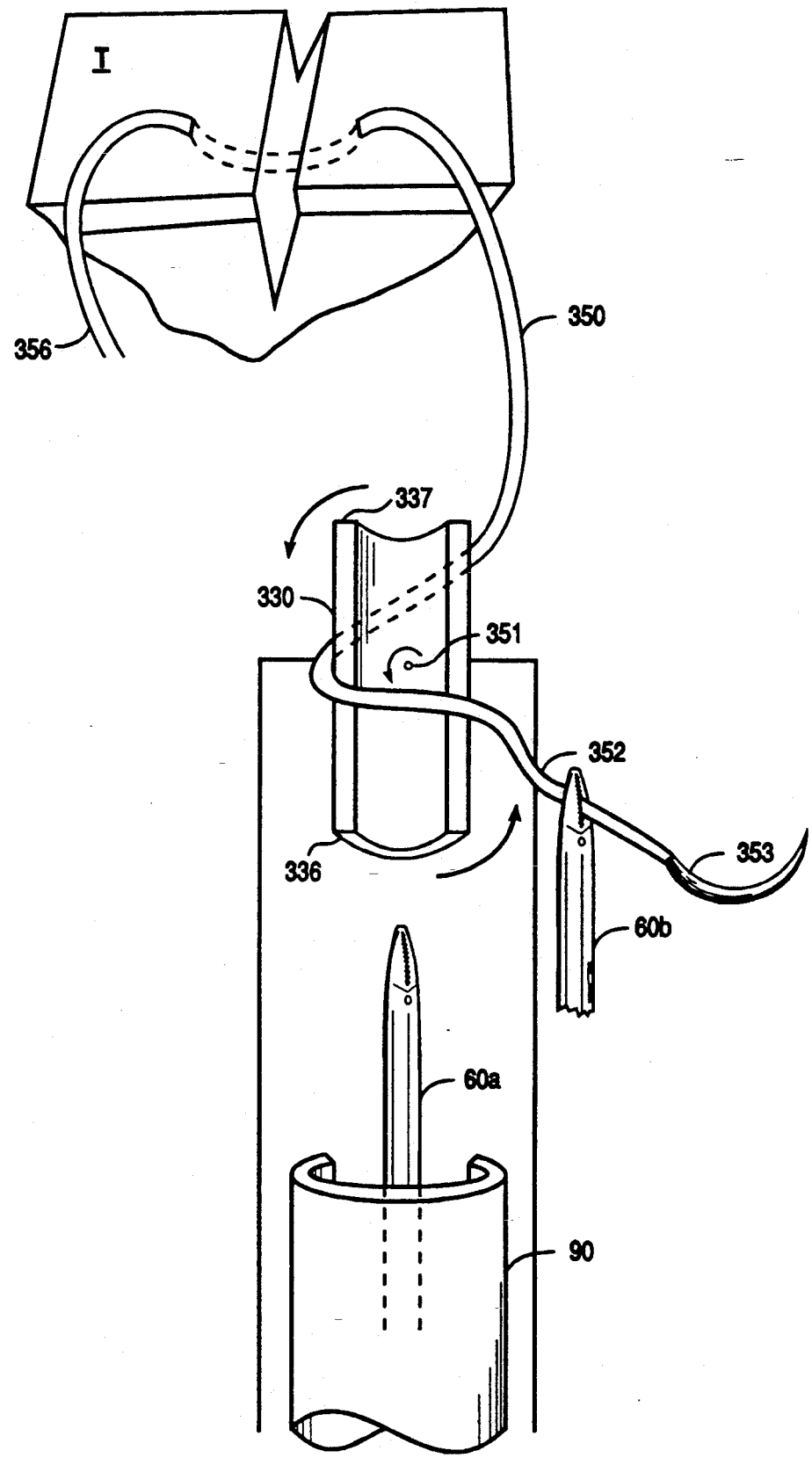
FIGS. 8A-C are lateral sections illustrating the formation of a knot with the embodiment of FIG. 7A.
Figure 8B:
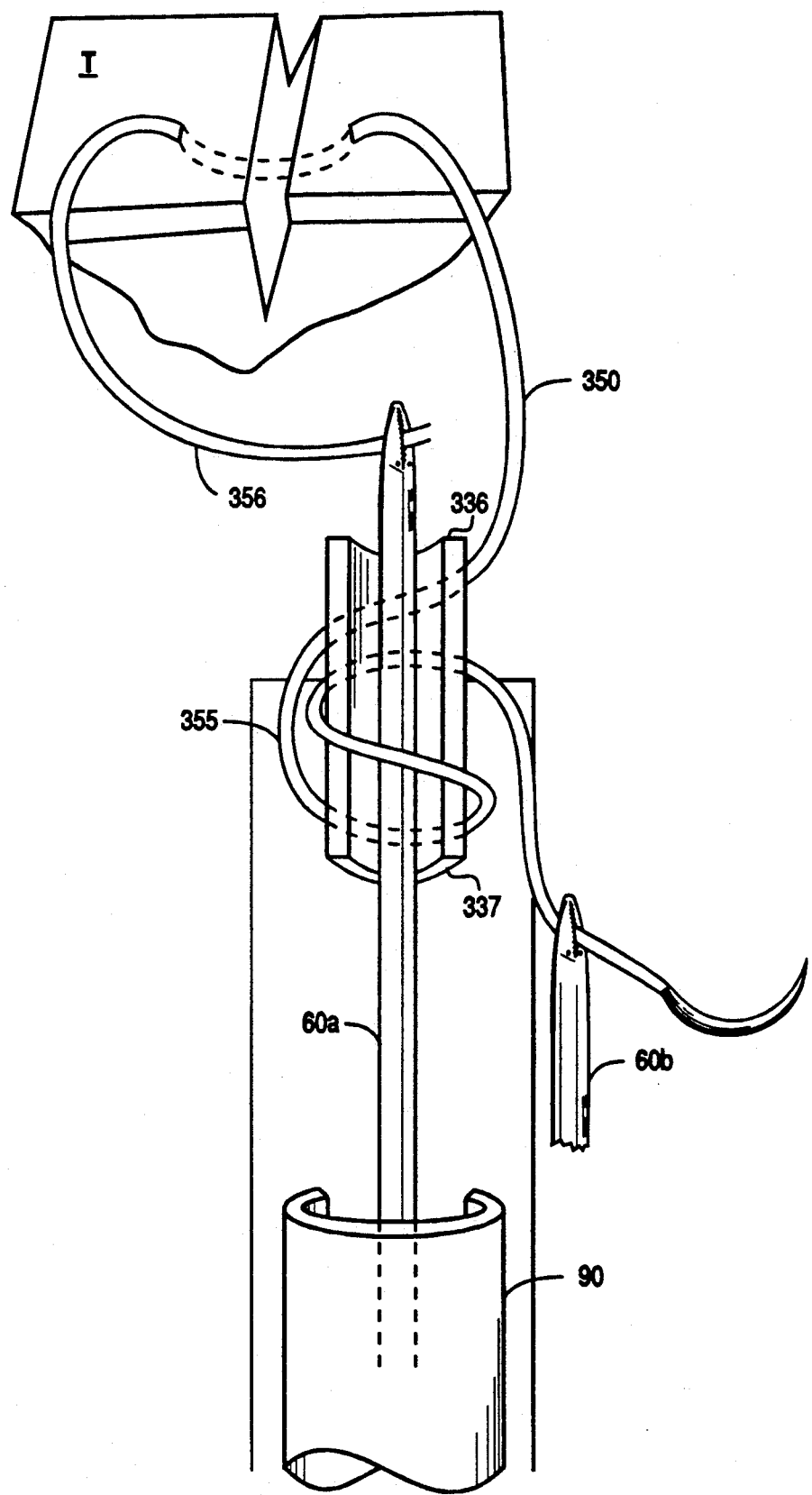
Figure 8C:
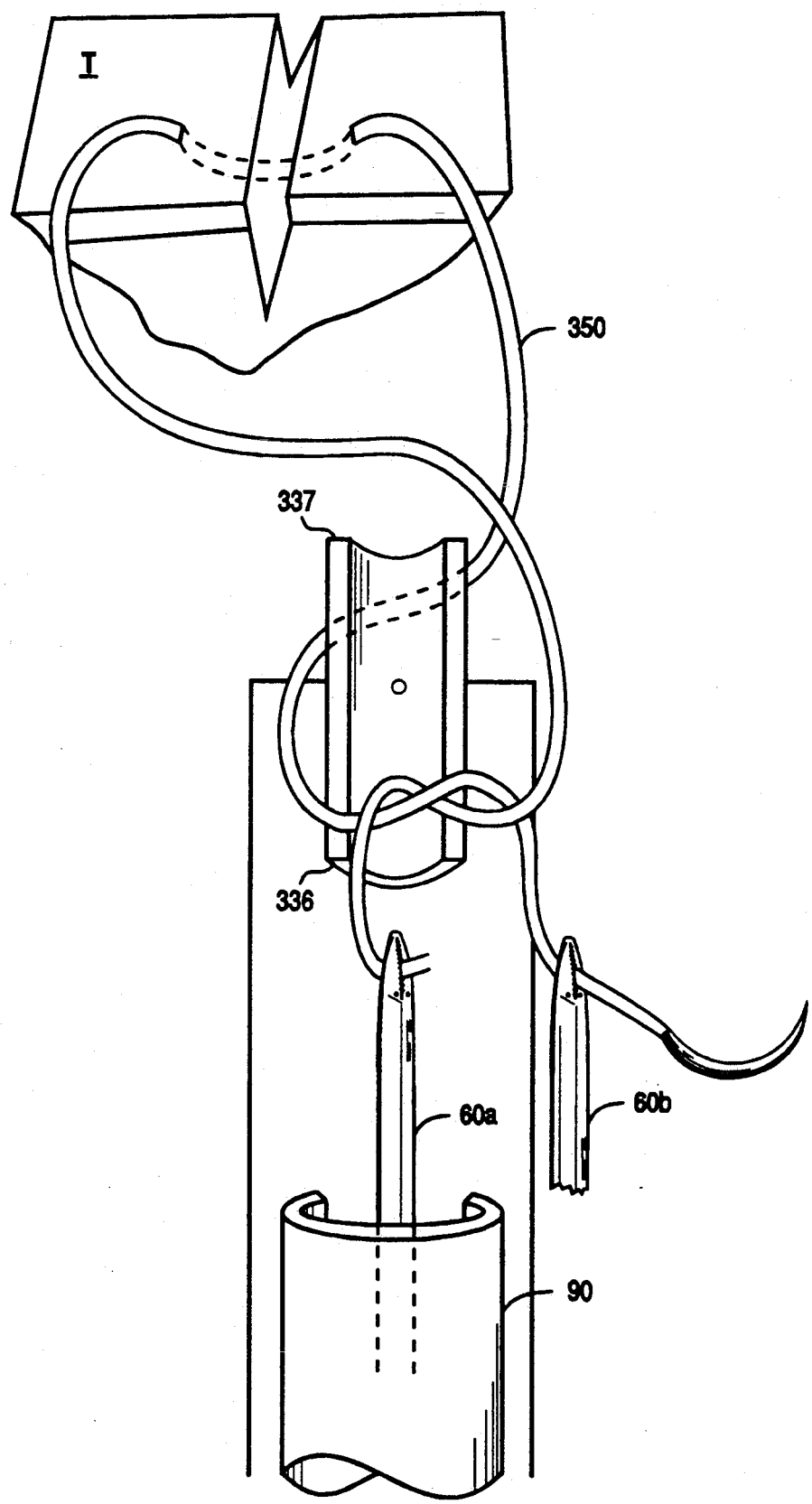

Referring to FIGS. 8A-C, the operation of device 3 will now be described. As shown in FIG. 8A, a suture 350 having a needle 353 has been driven through the tissue T, for example by supination of the needle 353 through the tissue T while the needle is held by the grasper 60b. Next, a needle-bearing segment 352 of the suture 350 is secured with the grasper 60b. Alternatively, the suture 350 may be secured by grasping the needle 353. Next, the suture 350 is looped around the trough 330, as shown. Trigger or lever (329 of FIG. 7A) is activated (e.g., with a finger) thereby rotating the trough 330 about 180 degrees (indicated by the movement of the proximal end 336 and the distal end 337 from FIG. 8A to FIG. 8B) for creating loop 355. Then the grasper 60a, which is disposed within the lumen of pusher 90, is advanced for grabbing the free end 356 of the suture 350. The free end 356 is then pulled through the trough 330 and loop 355, with the rotating trough then returned to its original position, as shown by the location of the proximal end 336 and the distal end 337 in FIG. 8C. Finally, the knot is completed by sliding the pushing shaft 90 forward towards the tissue surface.

Figure 9:
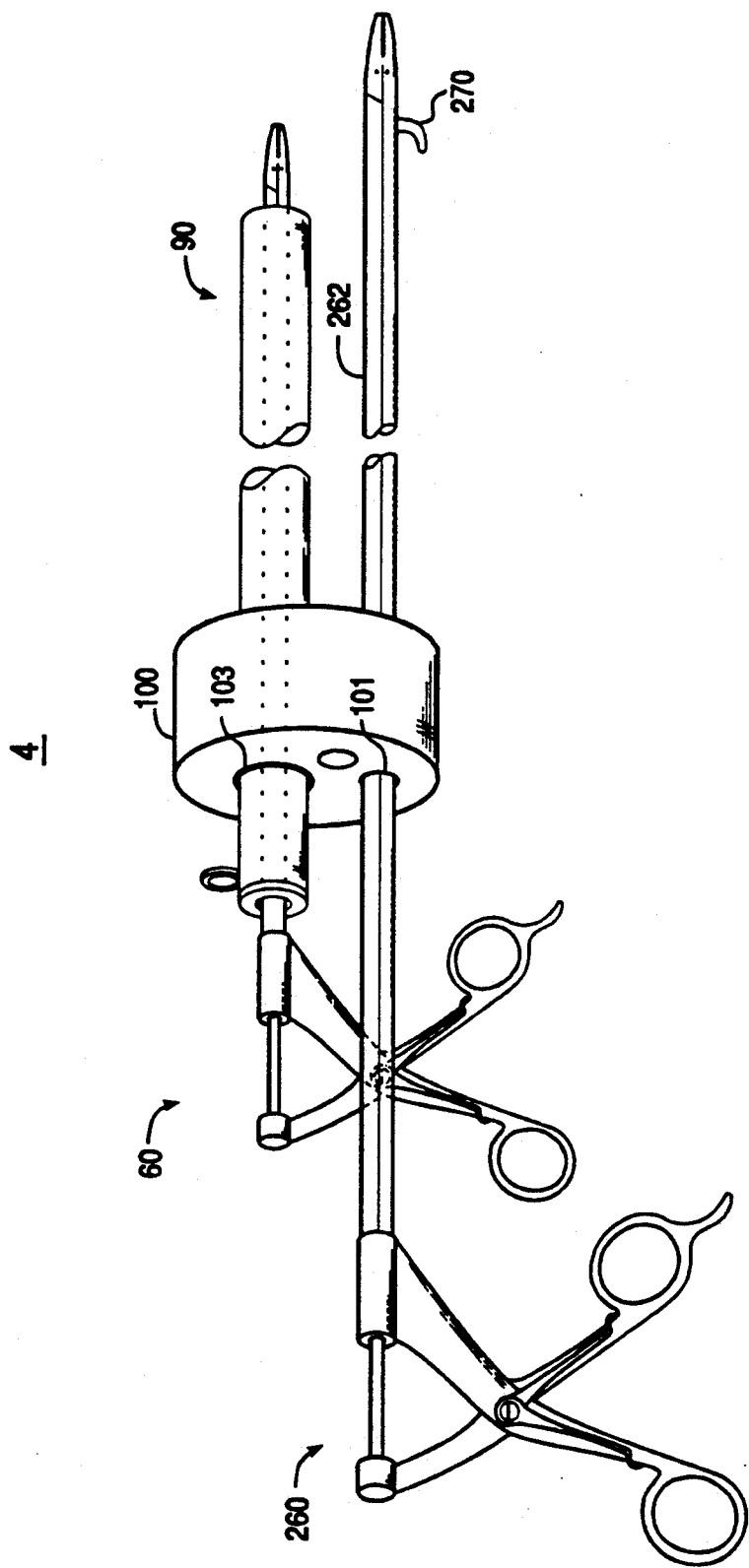
FIG. 9 is a lateral view of a fourth embodiment of the present invention.

Referring now to FIG. 9, a fourth embodiment of the present invention will be described. A suture applying and knot tying device 4 includes two graspers (one having a hook) and a pushing shaft. The device 4 may also include one or more adapters for stabilizing components.

The device 4 includes the following previously described components: grasper 60, hook-bearing grasper 260, and pushing shaft 90. In addition, device 4 may include adapter 100 for stabilizing the components as previously described.

As shown in FIG. 9, an exemplary configuration of the device 4 includes the pusher 90 and the grasper 60 disposed within the port 103 of the adapter 100, with the body of the grasper 60 disposed within the lumen of the pusher 90. Hook-bearing grasper 260 may be inserted through the port 101 of the adapter 100.

Figure 10A:
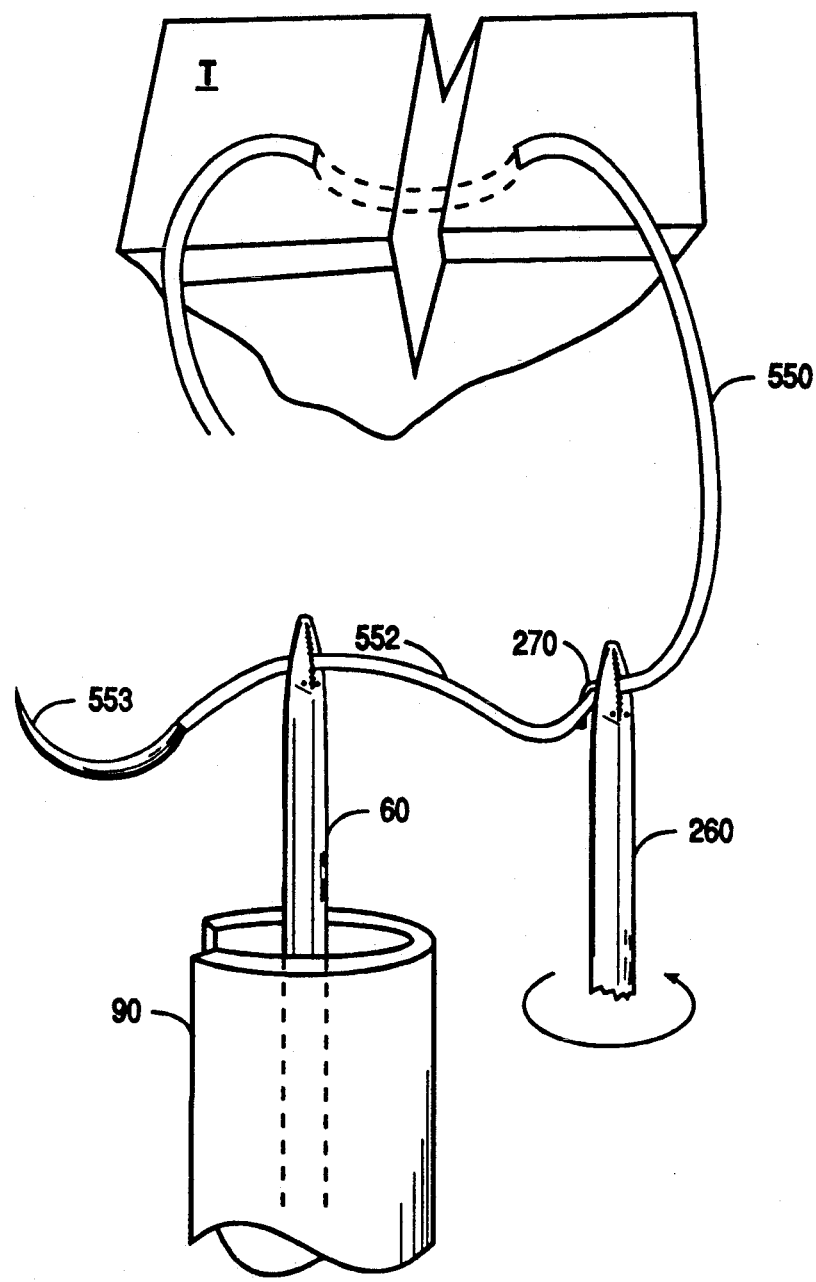
FIGS. 10A-B are lateral sections illustrating a technique for forming a knot with the embodiment of FIG. 9.
Figure 10B:
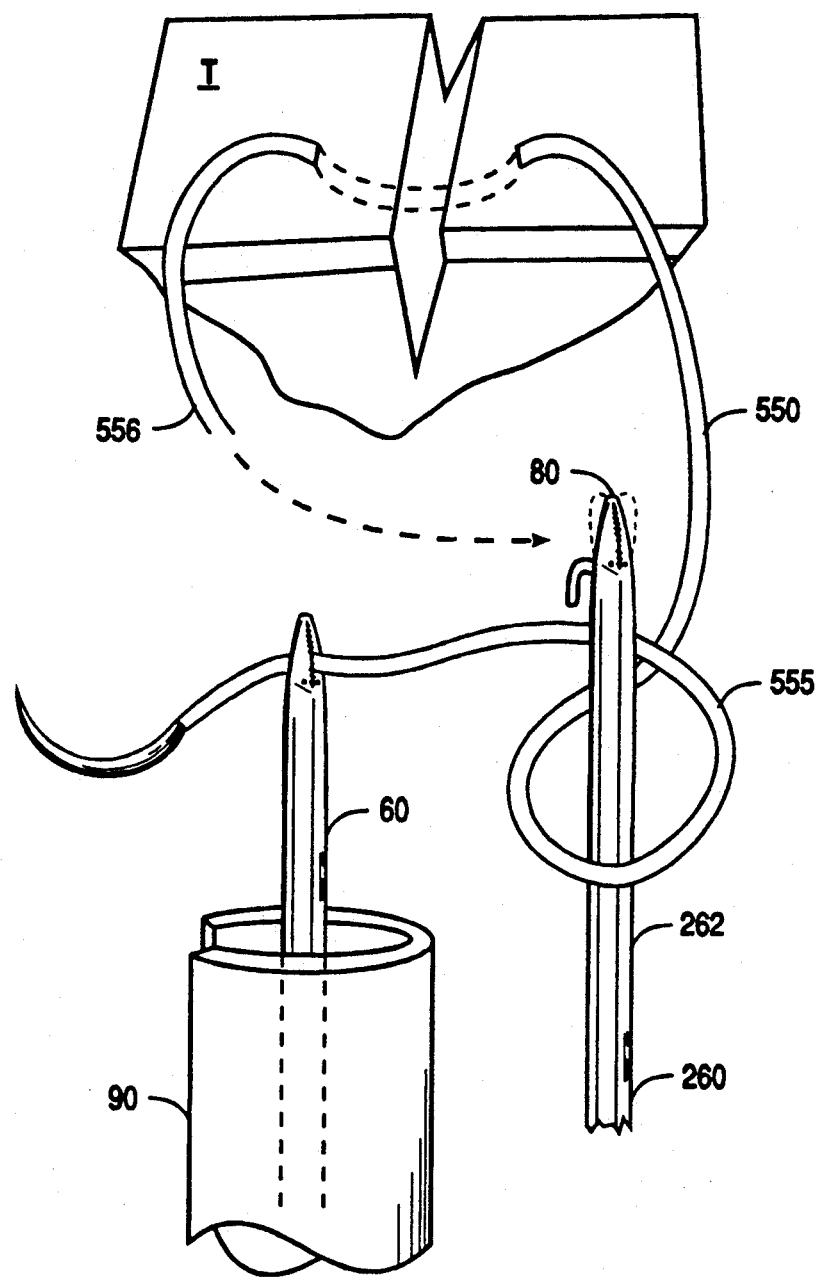

Referring now to FIGS. 10A-B, the operation of the device 4 will now be described. As shown in FIG. 10A, a suture 550 having a needle 553 has been driven through the tissue T, for example by supination of the needle 553 through the tissue T while the needle is held by the grasper 260. Next, a needle-bearing segment 552 of the suture 550 is secured with the grasper 60. Alternatively, the suture 550 may be secured by grasping the needle 553. Next, the hook-bearing grasper 260 is advanced and then retracted for snagging or capturing the suture segment 552 with the hook 270. As shown in FIG. 10B, a loop 555 is created by axial rotation of the grasper 260 while suture segment 552 is held by hook 270. Upon completion of rotation, the loop 555 surrounds the shaft 262 of grasper 260. While a loop may be formed around the hook 270 itself (and not around the shaft 262), a loop so formed would not be suitable for forming a knot. As the next step, the grasper 260, while its shaft 262 is within the loop 555, is advanced towards the free end 556 of suture 550. The grasping member 80 of the grasper 260 captures the free end 556, thus securing it to the grasper 260. Next, grasper 260 is retracted, thereby pulling the free end 556 through the loop 555. Finally, the knot is perfected by advancing the pushing shaft 90 forward towards the tissue.

While the invention is described in some detail with specific reference to a preferred embodiment and certain alternatives, there is no intent to limit the invention to that particular embodiment or those specific alternatives. Those skilled in the art will appreciate other applications within the scope of the present invention. The apparatus of the present invention may be adapted, for example, for use in laproscopic and arthroscopic instruments. Therefore, the true scope of the invention is defined not by the foregoing description but by the following claims.

What is claimed is:

1. A surgical thread applying and tying device comprising:
   a first grasping member including an elongate shaft having proximal and distal ends and means at the distal end for securing a length of thread;
   a second grasping member including an elongate shaft having proximal and distal ends and means at the distal end for securing the thread, forming a loop within the thread, and pulling a free end of the thread through said loop; and
   means disposed on the first grasping member for advancing the loop in a forward direction relative to the securing means.

2. The device of claim 1, wherein the advancing means comprises a cylindrical rod having proximal and distal ends and a central lumen extending therethrough, wherein the first grasping member is slidably received in the central lumen.

3. The device of claim 2, wherein the rod include a cutout along one side.

4. The device of claim 1, further comprising means on the second grasping member for flexing the distal end to deflect the thread securing means to facilitate loop forming by rotating the shaft about its axis.

5. The device of claim 1, wherein the first grasping means comprises an elongate shaft having proximal and distal ends, with pivotable jaws attached at the distal end and a handle attached at the proximal end.

6. A method for tying a knot in surgical thread comprising:
   a) securing a first end of the thread with a first grasping means;
   b) securing a length of the thread proximal to the first end with a second grasping means;
   c) axially rotating the second grasping means, thereby creating a loop in the thread;
   d) securing a second end of the thread with the second grasping means;
   e) pulling the second end of the thread through the loop, thereby forming a slip knot; and
   f) advancing the knot in a forward direction.

7. The method of claim 6, wherein step (b) includes
   advancing the second grasping means beyond a length of thread proximal to the first end;
   capturing the length of thread by retracting the second grasping means; and
   securing the captured length of thread to the second grasping means.

8. The method of claim 7, wherein the knot is advanced with a rod which is mounted coaxially with the first grasping means.

9. The method of claim 7, wherein the capturing step includes capturing the length of thread with a flexed end of the second grasping means.

* * * * *